United States Patent [19]

Willaman et al.

[11] Patent Number: 4,741,203

[45] Date of Patent: May 3, 1988

[54] TURBINE INSPECTION DEVICE AND ASSOCIATED COIL ASSEMBLY AND ASSOCIATED METHOD

[75] Inventors: Dwight O. Willaman, Ridley Park; George F. Dailey, Plum Boro; Michael J. Metala, Murrysville, all of Pa.

[73] Assignee: Westinghouse Electric Corp., Pittsburgh, Pa.

[21] Appl. No.: 933,707

[22] Filed: Nov. 21, 1986

[51] Int. Cl.⁴ ............................................ G01M 19/00
[52] U.S. Cl. ........................................ 73/116; 415/118
[58] Field of Search ............... 73/116, 866.5; 324/262, 324/219; 415/118; 356/241; 358/100, 106

[56] References Cited

U.S. PATENT DOCUMENTS

| | | | |
|---|---|---|---|
| 4,139,822 | 2/1979 | Urich et al. | 324/219 |
| 4,368,642 | 1/1983 | Carodiskey | 73/633 |
| 4,502,331 | 3/1985 | Singh et al. | 73/627 |
| 4,609,870 | 9/1986 | Lale et al. | 324/225 |
| 4,629,984 | 12/1986 | Scalese | 324/219 |

FOREIGN PATENT DOCUMENTS

| | | | |
|---|---|---|---|
| 2492527 | 4/1982 | France | 415/118 |
| 0627393 | 10/1978 | U.S.S.R. | 324/262 |

OTHER PUBLICATIONS

Photocopy of Manual, Lab Kit for Magnetic Shielding with AC Magnetic Pickup Probe, Copyright 1983.
Paper presented at EPRI Conference, Sep. 1986, San Antonio, Tex.

Primary Examiner—Michael J. Tokar
Assistant Examiner—Robert R. Raevis

[57] ABSTRACT

An inspection device which permits inspection of the interior of a turbine for metal integrity. The inspection device is mounted on a sensor assembly that engages a turbine blade and rests on the turbine disc. Metal integrity sensors are mounted on the sensor assembly and inspect various areas of turbine blades and turbine rotor steeples. The associated coil assembly provides a coil of wire and magnetic shielding which improves the sensitivity of the metal integrity sensors. The associated method provides for proper positioning of the apparatus and inspecting the turbine for metal integrity.

16 Claims, 5 Drawing Sheets

TURBINE INSPECTION DEVICE AND ASSOCIATED COIL ASSEMBLY AND ASSOCIATED METHOD

BACKGROUND OF THE INVENTION

1. Field of the Invention

The present invention relates to systems for turbine inspection, and, more specifically to a turbine inspection device that permits non-destructive evaluation of a turbine.

2. Background Information

High availability and reliability of power generation systems has been a major requisite of the electric utility industry for many years. The high cost of unreliability and forced outages is well known, and industry experience has shown blade distress to be a leading cause of turbine-forced outages. Distress incidents are attributable to a variety of mechanisms, including cyclic fatigue and stress corrosion. Many of these incidents and related turbine damage could be eliminated if a reliable non-destructive inspection system could be developed. Early detection of blade distress is important in preventing and minimizing lengthy turbine forced outages.

Current field inspection of turbines typically requires extensive turbine disassembly and component cleaning prior to the performance of non-destructive inspection. A further problem exists in finding a reliable and inexpensive method of evaluating high stress areas on a turbine blade. Experience has shown that the areas in a turbine most susceptible to cracking due to, among other reasons, cyclic fatigue or stress corrosion, are the trailing edge of the blade airfoil, the blade root, and the rotor steeple area of the turbine (the area where the blade root engages with the turbine). It is known that the trailing edge, from the transition region near the top of the platform for any prescribed distance above the platform, is most prone to cracking. As for the turbine blade root and the turbine rotor steeple, the exit face surface area of those components is most prone to cracking. As is known to those skilled in the art, cracks are initiated and are visible on the turbine blade and turbine rotor steeple surfaces.

When turbine blades are removed for inspection, examination for cracks is done by fluorescent magnetic particle testing. This involves sandblasting the turbine blade to remove any scale build up which may have occurred during turbine operation and applying a magnetizing field to the blade with the aid of a magnetizing yoke coil or prod. Fluorescent magnetic particles suspended in a liquid vehicle are applied to the test surface. Cracks in the blade disrupt the magnetic field creating a leakage site which attracts the tiny suspended particles. A "black" light is used to facilitate the inspection. Crack lengths can then be measured and compared to calculated allowable critical crack lengths. Depending on the results from the fluorescent magnetic particle test, the blades may then be replaced as necessary.

This method of turbine inspection, where turbine blades are removed from the turbine rotor steeple, is both time consuming and expensive. Also, good blades may possibly be damaged when being removed or inserted into the turbine. Damage to rotor steeples is also possible during blade removal.

It is also known to inspect a turbine by placing a piece of conduit, with an eddy current coil sensor and/or a small television camera fastened to one end of the conduit, inside a turbine. The operator manually probes the turbine test areas, using the camera to help place the eddy current coil on the area to be inspected. Problems with this type of device include inaccurate positioning of the eddy current coil on the area to be inspected and failure to adequately inspect all critical areas where cracks may be present within the turbine. This can lead to missed or future calls resulting in damage to the turbine and replacement of the turbine blades.

Accordingly, there exists a need for a turbine blade inspection system which permits non-destructive inspection of turbine blades and turbine rotor steeples while overcoming the disadvantages of presently used methods. Further, the system should provide for rapid assessment of blade and rotor steeple metal integrity during a brief unit shutdown and in highly confined spaces, be inexpensive and simple to use, and pose minimal safety and health risks.

SUMMARY OF THE INVENTION

The present invention provides a turbine inspection device which includes a support assembly apparatus, sensor apparatus on the support assembly apparatus for inspecting the turbine for defects and a blade root sensor on the support assembly apparatus which is adapted to follow the serrated contour of an edge of a turbine blade root for inspecting a blade root of the turbine with the support assembly apparatus having attachment apparatus for engaging a portion of the turbine thereby positioning the sensor apparatus and the blade root sensor to facilitate inspection of the turbine and a blade root of the turbine.

Also provided is a method for inspecting turbines which includes providing a turbine inspection device which includes support assembly apparatus, sensor apparatus on the support assembly apparatus for inspecting the turbine for defects and a blade root sensor which is adapted to follow the serrated contour of an edge of a turbine blade root for inspecting a blade root of the turbine with the support assembly apparatus having attachment apparatus for engaging a portion of the turbine thereby positioning the sensor apparatus and the blade root sensor to facilitate inspection of the turbine, positioning the support assembly apparatus on the turbine, inspecting the turbine with the sensor apparatus, inspecting a blade root of the turbine with the blade root sensor and receiving data from the sensor apparatus and the blade root sensor relative to the inspection of the turbine and the blade root of the turbine.

Additionally, a turbine inspection device is provided which includes support assembly apparatus which includes attachment apparatus for engaging a blade of the turbine, a blade root sensor slidably mounted on the support assembly apparatus and adapted to be movable along a cam defined by the support assembly apparatus and movable along a serrated edge of the blade root of a blade of the turbine to be inspected when the support assembly apparatus is engaged with the blade of the turbine. Also provided are positioning cables which cooperate with the support assembly apparatus and the blade root sensor for effecting the movement between the support assembly apparatus and the blade root sensor with the blade root sensor including output apparatus for providing data relative to the inspection of the blade root of a blade of the turbine by the blade root sensor.

BRIEF DESCRIPTION OF THE DRAWINGS

The invention may be better understood, and further advantages and uses thereof are readily apparent, when considered in view of the following detailed description of exemplary embodiments, taken with the accompanying drawings in which.

DETAILED DESCRIPTION OF THE PREFERRED EMBODIMENTS

Figure 1:
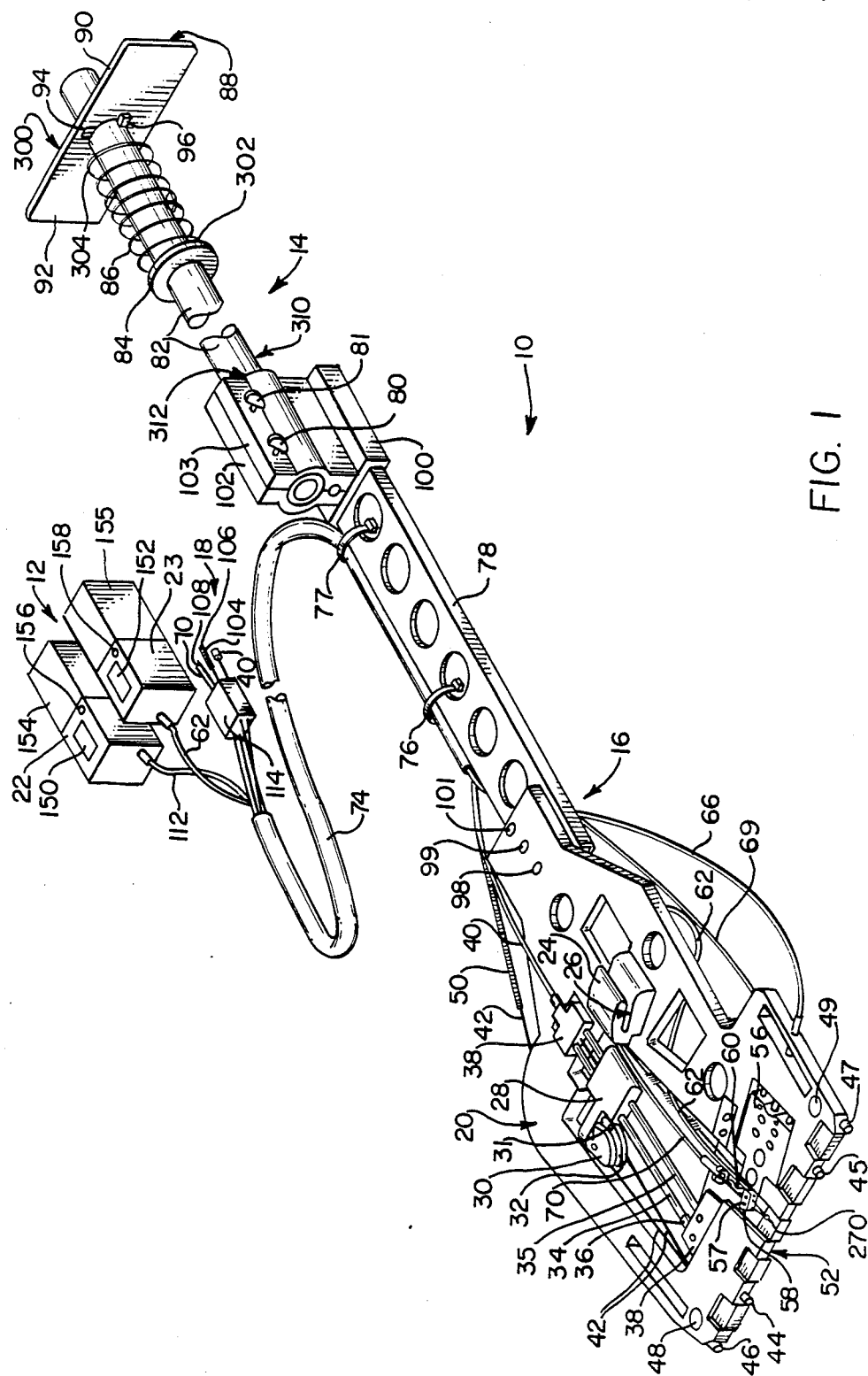
FIG. 1 is an isometric view of the turbine inspection system, constructed according to the provisions of the present invention.

FIG. 1 shows a turbine inspection device that is used to inspect turbine blades and the rotor steeple, or rotor steeple, area of a turbine. The inspection device includes, generally, a sensor assembly and a support assembly which engages a portion of the turbine and positions the support assembly on the turbine. A data acquisition system, which is a subassembly of the sensor assembly, permits electrical signals generated by the turbine inspection device to be recorded for real-time or post-inspection analysis.

The sensor assembly also includes sensors that perform metal integrity testing on various internal parts of a turbine. For example, the sensor assembly may be placed within a turbine to test the metal integrity of a turbine blade or of the turbine blade root. Additionally, the rotor steeple, or rotor steeple, area can be tested. The rotor steeple area is that area where turbine blade roots engage with the turbine and is an extension of the turbine disc. The metal integrity testing involves surface analysis of the test part to determine the presence of service-induced cracks or pits on the turbine blade root, the airfoil trailing edge of a turbine blade, and on the rotor steeple, or rotor steeple, area of a turbine as these areas are prone to cracking.

Prior to inspection, man-hole covers, at convenient locations on the outer cylinder of the turbine, are removed, exposing the inner cylinder of the turbine. Access ports are removed from the inner cylinder, permitting access to the turbine blades and turbine rotor steeple. Once access to the turbine interior is accomplished, placement of the inspection device on the turbine blade and turbine rotor steeple can commence. It should also be noted that, once the interior of the turbine is exposed, a camera may be placed within the turbine to facilitate visual inspection and blade calibration instrumentation can be introduced into the turbine (not shown). Such a camera is preferably manufactured by the Welch-Allyn Company and sold under the trademark "VIDEOPROBE", and is preferably mounted on the sensor assembly (not shown).

It is also contemplated that a fiberscope may be employed to visually inspect the turbine (not shown), and would be attached to the support assembly using known means. Preferably such a fiberscope would be any one of a variety of fiberscopes manufactured by Olympus, Inc.

As is known in the art, a turbine is divided into two sectors, a right-hand sector and a left-hand sector. Therefore, a right-hand sensor assembly is needed for the right-hand sector and a left-hand sensor assembly is needed for the left-hand sector. As the left-hand and right-hand sectors are mirror images of each other, the sensor assemblies, likewise, are mirror images of each other.

Once the turbine interior is exposed, the operator performing the metal integrity inspection manually places one of the sensor assemblies into the turbine interior between two rows of turbine blades which encircle the turbine rotor steeple, and which are positioned on the turbine disc. The sensor assembly has a blade guide that fits over the trailing edge of a turbine blade and ensures proper tangential alignment of the sensor assembly relative to the trailing edge of a turbine blade. If such alignment is not accomplished, incorrect evaluation of the turbine blade will occur.

As the sensor assembly guide engages the trailing edge of a turbine blade, one of the metal integrity sensors mounted on the sensor assembly engages the trailing edge of another turbine blade. That turbine blade is once removed from the turbine blade on which the guide is engaged. While proper alignment of the upper part of the sensor assembly on the trailing edge of a turbine blade is ensured by the blade guide, the lower part of the sensor assembly must be properly aligned, otherwise proper placement of the entire sensor assembly will not be accomplished. Radial alignment of the lower part of the sensor assembly on the turbine disc is confirmed by two switches, one placed on each end of the bottom edge of the sensor assembly.

When properly placed on the turbine disc, two light indicators, one for each switch, are activated, indicating correct alignment or seatment, of the sensor assembly on the turbine disc. To maintain perpendicularity of the sensor assembly once it is placed over the trailing edge of a turbine blade and radially aligned on the turbine disc, permanent magnets are mounted on the lower part of the sensor assembly. Because of their positioning, the magnets engage with the blade rotor-root steeple region of the turbine.

Located also in the lower part of the sensor assembly is another metal integrity sensor. This sensor can test the metal integrity of various areas of the blade rotor-root steeple region. This sensor, unlike the sensor for the trailing edge, traverses the serration region of the blade rotor-root steeple region, that is, the region where, for example, the concave side of a blade root engages with a convex side of the rotor steeple. This engagement occurs when a turbine blade is mounted on the rotor steeple.

Once the sensor assembly is properly placed in the turbine, the operator engages the positioning assembly with the upper part of the sensor assembly. The positioning assembly, which can be spring loaded, is placed into the interior of the turbine and rests against the interior wall of the turbine inner cylinder. Once the positioning assembly engages the sensor assembly and the interior wall of the inner cylinder, proper alignment of the sensor assembly is fixed for the duration of testing that area of the turbine. This also permits the operator to use both hands to control sensor movement with the controller assembly and perform other tests, if necessary, thereby minimizing operator fatigue due to holding the sensor assembly during testing. Once the area is tested, the sensor assembly and positioning assembly can be removed, by reversing the above procedure, and placed at another test area within the turbine.

The controller assembly controls the movement of the sensors. The trailing edge sensor sits in a sensor holder and slides from the transition region just above the blade platform, the turbine blade-turbine blade root area, up towards the top of the turbine blade when the operator pulls the appropriate cable on the controller assembly. The trailing edge sensor holder is spring loaded so, when the top of the trailing edge is reached, the operator can release the cable and the sensor will return to its start position. The trailing edge sensor is also spring loaded within the sensor holder to ensure continuous engagement of the trailing edge sensor on the blade trailing edge.

The metal integrity sensor for the turbine blade root-turbine rotor steeple region operates slightly differently. The sensor that tests the turbine blade root-turbine rotor steeple region sits in a cam assembly mounted on the lower part of the sensor assembly. A cam, mounted in the cam assembly, traces the turbine blade-root serration area or turbine rotor steeple serration area. The active head of the sensor is spring mounted in the sensor so lift off and edge effects, which would cause false readings, are minimized. The sensor, mounted in the cam on a bearing, is pulled by an extraction cable from its start position, the base of the turbine blade root, to its end position, the top of the turbine blade root. This sensor is not spring loaded within the cam or cam assembly, and a retraction cable is pulled to bring the sensor from its end position back to its start position.

The extraction cable or retraction cable may be connected to a series of springs. One end of the spring series is mounted to the sensor assembly frame and the other end is connected to either one of the cables in an area removed from where either cable is attached to the sensor. If an actual crack or defect is detected, the operator can stop pulling the sensor and the sensor will remain at the actual crack position. While it is important to know that an actual crack exists, it is equally important to know the length of the crack on the blade root.

The cam assembly is mounted on a spring-loaded probe. When an actual crack is found, the operator can stop moving the sensor by releasing the extraction cable, or the retraction cable, depending on the test direction. The operator uses a vernier assembly to move the probe cable, which causes the entire cam assembly to shift perpendicular to the blade root serrations, or rotor steeple serrations, along an imaginary line tangent to the serrations. Since the probe cable is controlled by a vernier, the crack length can accurately be determined. If necessary, the operator can pull the extraction cable or the retraction cable in conjunction with the vernier controlled probe cable in order to determine linearity or non-linearity of the crack.

Another important feature of the slider assembly is the ability to adjust the root probe cam assembly to move it nearer to or farther away from the blade root/steeple interface to minimize edge effects, which would cause missed or false readings. As known in the art, eddy current probe signals can be adversely affected by proximity to edges or other geometric discontinuities.

If one of the cables which controls the movement of the sensor is not engaged with a series of springs, when the cam assembly is moved perpendicularly, the sensor will move from its stopped position, causing the operator to lose position of the crack. Without the springs, the cables would be loose, causing the sensor to move from its stopped position. The loose cables would also be prone to entanglement with the other cables mounted on the sensor assembly.

The sensors include a data acquisition system which can gather, display, and store test data. Each sensor may have its own test instrumentation, or may be used with a multiple channel eddy current test instrument, and all test instrumentation is connected to a magnetic tape recorder for permanent recordation of data. A computer may also be used to gather, analyze, store and display the inspection data. As the data, for example, voltage signals, are displayed, the operator or an assistant would be able to detect the presence of an actual crack or defect and determine its length.

The sensor assembly is not limited only to sensors that determine the integrity of a turbine blade trailing edge and the integrity of a turbine blade root or rotor steeple. Sensors can be mounted in cam assemblies, similar to the one discussed above, except that a slider assembly is not necessary to move the cam assembly in order to determine crack length. The top of each cam assembly, preferably, is pivotally mounted to the sensor assembly frame. The bottom of each cam assembly is connected to a control cable by a series of pulleys and springs. The cam assemblies are mounted on the pivot points such that the cams on which the sensors travel align with the various concave serration regions or convex serration regions of the blade root or turbine rotor steeple to be inspected.

For example, the cam assemblies can be arranged on the sensor assembly such that, when the sensor assembly is properly mounted within the turbine, the concave serration region of a rotor steeple engaged with the blade root of a first turbine blade, the concave serration region of a blade root of a turbine blade once removed from the first turbine blade, the convex serration region of a blade root of a turbine blade twice removed from the first turbine blade, and the convex serration region of a rotor steeple engaged with the blade root of a turbine blade thrice removed from the first turbine blade may be inspected. Other arrangements of the cam assemblies are possible. If an actual crack is located by any of the sensors, the cam assembly, related to that sensor, can be moved perpendicular to the corresponding serration region along a line tangent to the serration to determine the actual crack length. This is accomplished by manipulating a cable connected to the bottom of the cam assembly, that is, the end distal from the pivot point. The pulleys and springs discussed above ensure smooth and proper perpendicular movement of the cam assembly.

The details of the turbine blade inspection assembly shown in FIGS. 1 through 4 are presented below.

FIG. 1 shows an isometric view of the turbine inspection assembly, which includes support assembly 10, and positioning assembly 14, sensor assembly 16 and controller assembly 18. Data acquisition systems 22 and 23 send and receive electrical signals, through cables 112 and 62, to and from upper sensor 31 and lower sensor 58, respectively, and display the voltage signal on screens 150 and 152, respectively. Data storage units 154 and 155 store data received by data system 12 for real-time or post-inspection analysis. Also shown is data system 12, which may range in complexity from an oscilloscope to a computer. Also, data storage units 154 and 155 could range in complexity from a tape recorder to floppy or hard disc drives. Software programs to run data system 12, if necessary are widely marketed for purchase or may be readily constructed by one of ordinary skill in the art.

Figure 2:
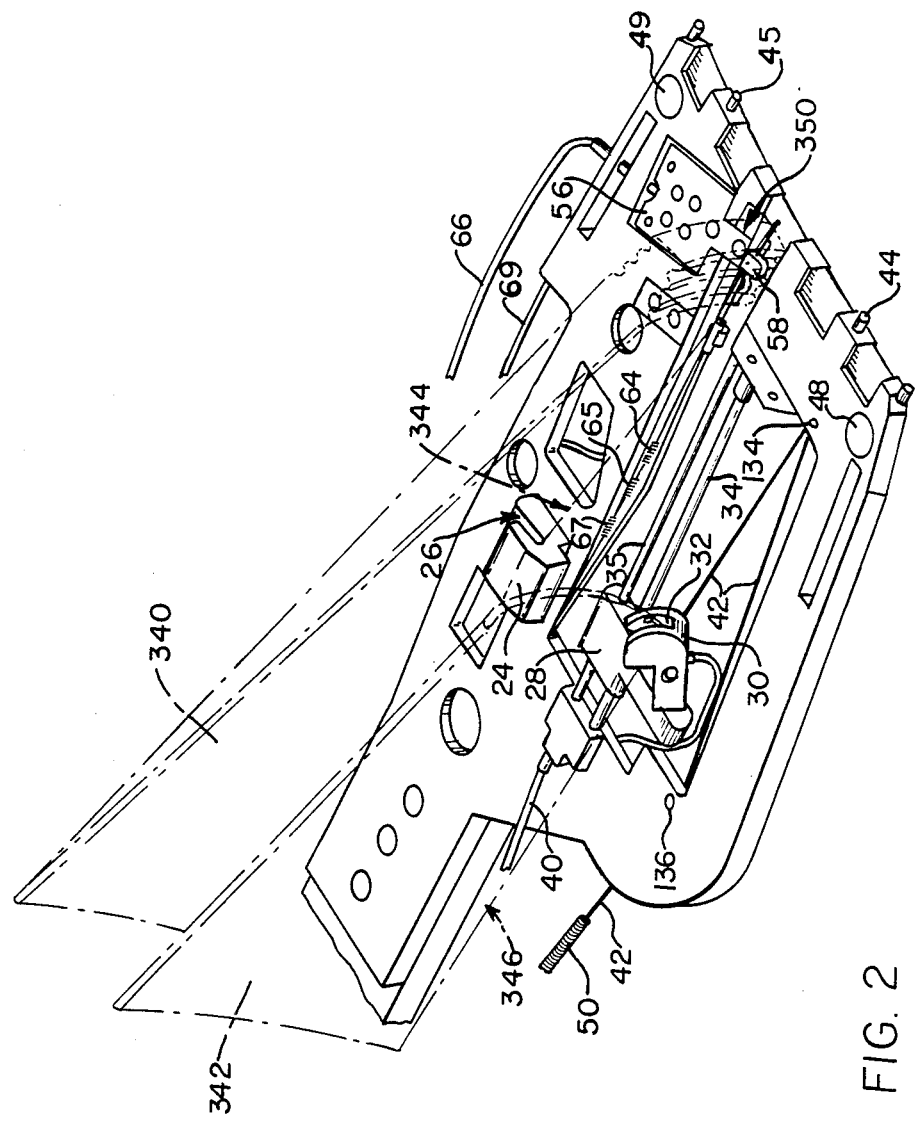
FIG. 2 is a partial isometric view of the turbine inspection system shown in FIG. 1 engaged with turbine blades of a turbine.
Figure 3:
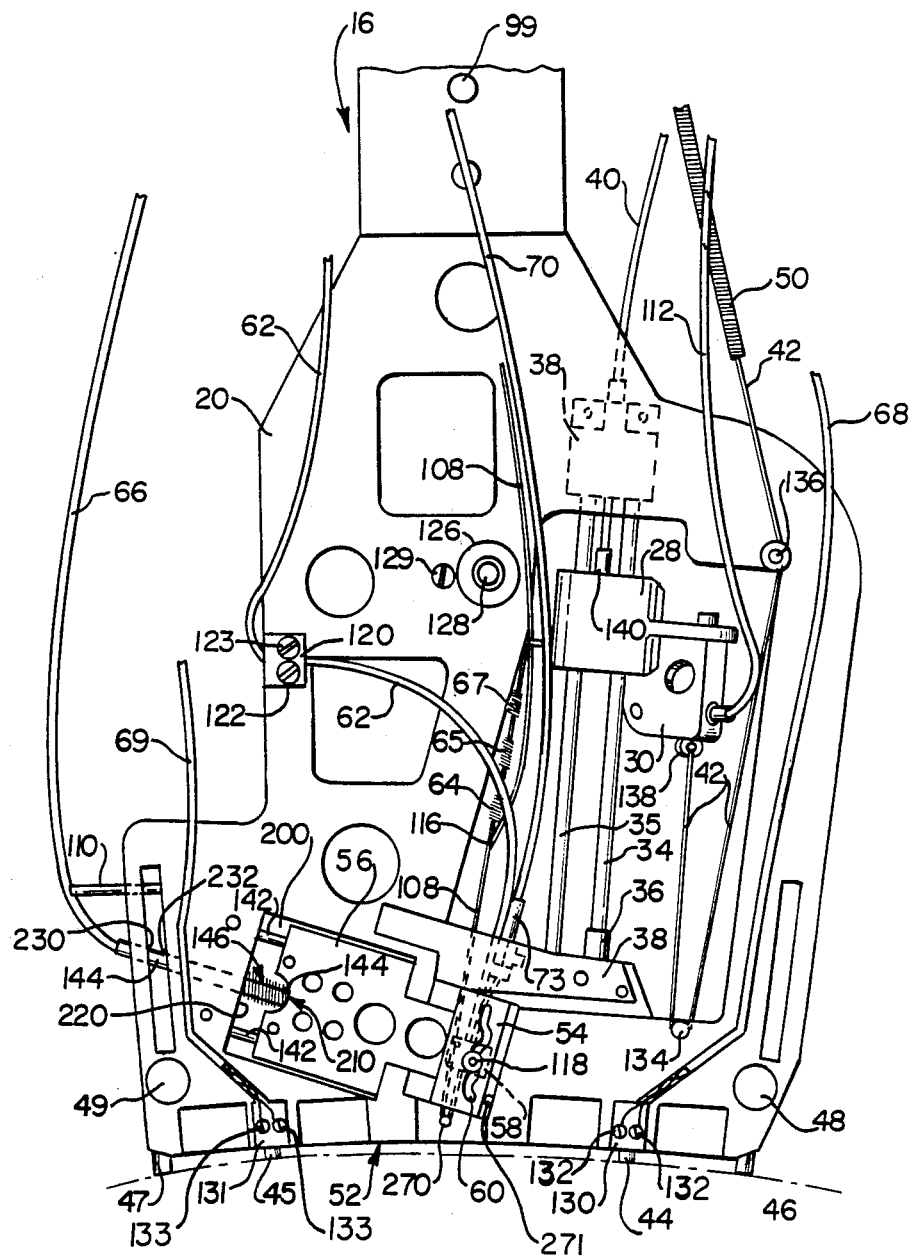
FIG. 3 is a partial rear view of the sensor assembly shown in FIG. 1.
Figure 4:
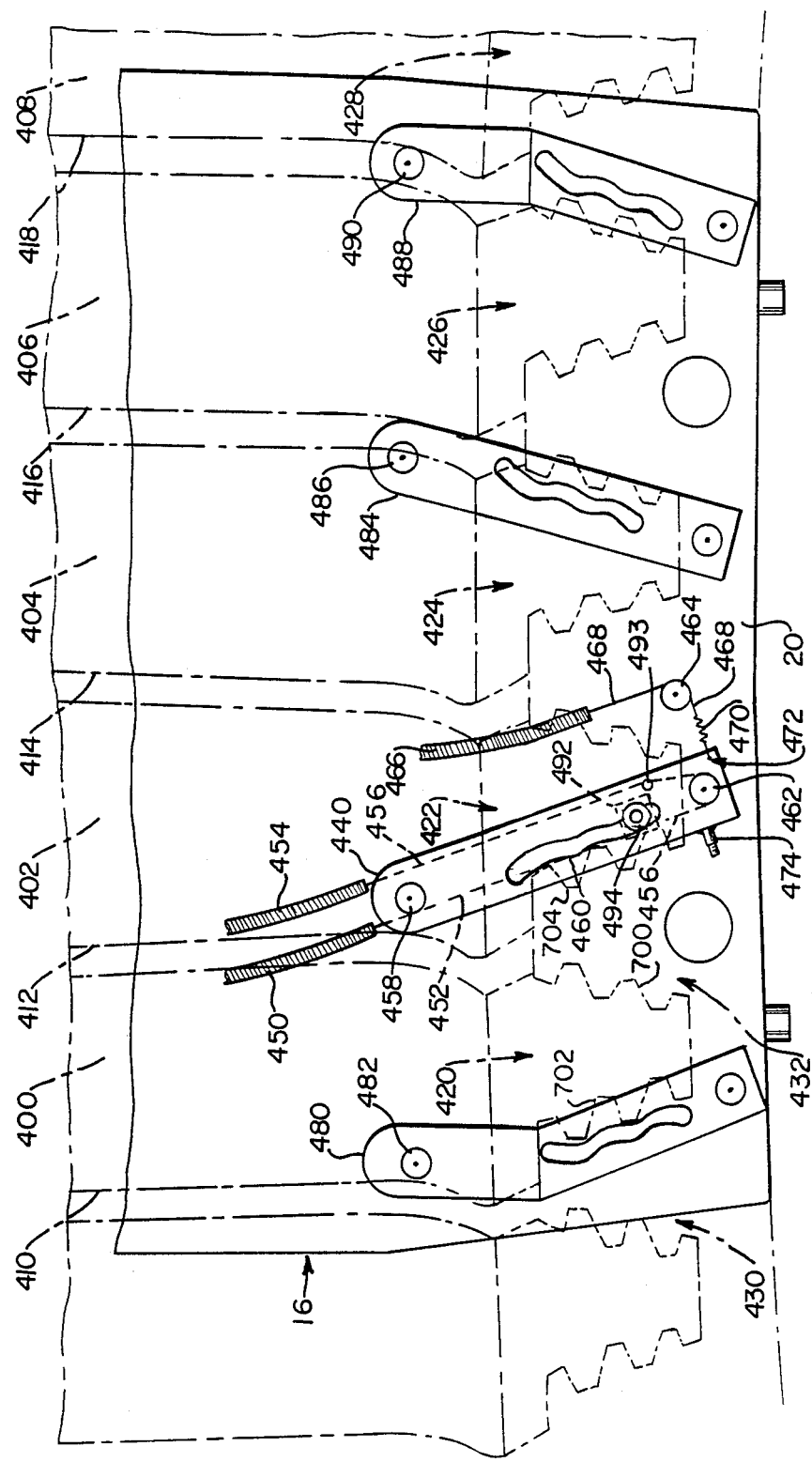
FIG. 4 is a partial schematic view of a turbine inspection system, constructed according to the provisions of the present invention.

FIG. 2 shows sensor assembly 16 mounted on turbine blade 340. Blade guide 24, which ensures proper initial placement of sensor assembly 16, is held in place by washer 126 and bolt 128 (FIG. 3). Shoulder screw 128 permits free pivoting of blade guide 24 so that the trailing edge of a turbine blade fits properly into slot 26 of blade guide. Fastener 129 fits into blade guide 24, limiting the pivoting action. Trailing edge 344 of blade 340 engages within slot 26 of blade guide 24 to deliver the upper and lower portions of sensor assembly 16 into the turbine in a position, as shown in FIG. 4, which is in contact with blade roots 420, 422, 424 and 426 and rotor spindles 430 and 432. As slot 26 of blade guide 24 initially engages trailing edge 344 of blade 340, slot 32 of probe holder 30 engages with trailing edge 346 of blade 342. This arrangement further helps to properly position sensor assembly 16 into the turbine.

Referring to FIG. 3, to ensure that edge 52 is properly distanced from the disc, switches 130 and 131 are mounted within edge 52 by fasteners 132 and 133, respectively. Each of switches 130 and 131 operate independently and sends a signal back to data system 12 through wires 68 and 69, respectively, when one or both sides of edge 52 is properly distanced from the turbine disc. Wires 68 and 69 are mounted within frame 20 of sensor assembly 16 to prevent entanglement with sensor control cables 62 and 112. When probe 44 of switch 130 touches the turbine disc, contact is made, sending a respective signal back to data system 12. When switch 130 is closed, indicator light 156 is activated, indicating edge contact. When switch 130 is open, indicator light 156 is deactivated, indicating no edge contact. This arrangement is the same for other switch 130 and indicator light 158.

The distance between switches 130 and 131 on edge 52 is such that, when slot 26 of blade guide 24 and probe holder 30 engage their respective trailing edges 344 and 346 of blades 340 and 342 (FIG. 2), switches 130 and 131 will indicate contact on the turbine disc only when the proper alignment is obtained. To further ensure and maintain proper alignment of sensor assembly 16, magnets 48 and 49 are mounted on the lower part of sensor assembly 16 and draw sensor assembly 16 to the blade rotor-root steeple area of a turbine. Rests 46 and 47 are screwed in either end of edge 52 so that they can be raised or lowered within frame 20 to ensure proper distancing of edge 52 from the turbine disc.

Once the operator has placed sensor assembly 16 on the turbine blade and has correctly aligned sensor assembly 16 using blade guide 24, magnets 48 and 49 and switches 130 and 131, the operator can secure sensor assembly 16 to the interior wall of the turbine inner cylinder by using positioning assembly 14. Positioning assembly 14 has two ends, active end 300 and passive end 310. Passive end 310 includes shaft 82 which engages with the upper part of sensor assembly 16 by being received within opening 312. Opening 312, formed by shaft receiving portions 102 and 103 is appropriately sized and shaped to receive shaft 82 of passive end 310. Fasteners 80 and 81 draw shaft receiving portions 102 and 103 in tight contact with shaft 82 of passive end 310 thereby securing shaft 82 into place. Active end 300 of positioning assembly 14 includes spring 86 and plate 90. Spring end 302 is engaged with ring 84 of active end 300. Spring end 304 is engaged with rear face 92 of plate 90 such that, when passive end 310 is engaged the upper part of sensor assembly 16, front face 88 of plate 90 will engage the access opening of the turbine inner cylinder(not shown). Assembler pad (not shown) is placed on face 88 of plate 90 so that slippage will be prevented.

Bar 78, which is part of sensor assembly 16, is attached at the top of sensor assembly 16 by fasteners 98, 99 and 101. The end of bar 78, distant from sensor assembly, is sized to permit base 100, to which shaft receiving portions 102 and 103 are attached by fasteners (not shown), to slide on. Tubing 74 contains the sensor and control cables so as to prevent entanglement within the turbine and during operation of device 10. Ties 76 and 77 hold tubing 74 to bar 78.

Once sensor assembly 16 is held in place by positioning assembly 14, metal integrity testing can be performed. Generally, two areas of a turbine blade are normally inspected; the trailing edge of a turbine blade and the turbine blade root. However, it may be desirable to reposition lower sensor 58 thereby allowing the rotor steeple area of the turbine to be inspected separately or in conjunction with the blade root of a turbine blade.

Upper sensor 31, which is spring-mounted within probe holder 30, is held in continuous contact with trailing edge 346 of blade 342. Probe holder 30 is mounted on shafts 34 and 35 by probe holder mount 28. Probe holder mount 28 rests on spacer 36 which is in turn, mounted on shaft 34, to ensure proper start position for probe holder 30, and thus sensor 31, on trailing edge 346. Shafts 34 and 35 are mounted on frame 20 of sensor assembly 16 by mounting blocks 38, such that, when the operator causes probe holder mount 28 to move by pulling cable 40, probe holder 30 will be able to traverse trailing edge 346 without twisting, and therefore without jamming probe holder 30 on trailing edge 346, thereby eliminating a potential source of error in testing blade 342 due to lift-off effects.

Cable 112 electrically connects sensor 31 to data system 12. Cable 40, which controls the movement of probe holder mount 28 and probe holder 30 across trailing edge 346 is fastened to the top of probe holder mount 28 at connection 140. The first end of spring 50 is fastened to the upper part of frame 20 by ordinary means.

The second end of spring 50 is fastened to the second end of cable 42 by ordinary means. The first end of cable 42 is then fastened to the bottom of probe holder mount 28 at connection 138, after first passing through pulleys 134 and 136, which are mounted on frame 20. When cable 40 is pulled and probe mount holder 28 moves, cable 42 moves in the opposite direction as holder 28, causing tension on spring 50. When testing is complete and cable 40 is released, spring 50 contracts, causing cable 42 to return probe holder mount 28 to its start position. The arrangement ensures proper placement of probe holder 30 after the operator has caused sensor 31 to traverse trailing edge 346.

Lower sensor 58 is mounted in cam assembly 54 and travels along cam 60 such that active head 57 of sensor 58 faces outwardly on the same face of frame 20 where guide block 24 is mounted. Active head 57 is spring (not shown) mounted within sensor 58 to prevent lift off of active head 57 from the area being tested. Lift off of active head 57 from the area being tested would cause erroneous inspection of the area to occur. Cam assembly 54 is further mounted to slide assembly 56, which, in turn is mounted on shafts 142. When sensor assembly 16 is properly mounted within a turbine, cam assembly 54 and, therefore, cam 60 are aligned so that sensor 58 can travel over cam 460 (See FIG. 4). It may be appreciated by those skilled in the art, however, that the alignment of cam assembly 54 could be so as to permit sensor 58 to travel over the convex serration region of blade root 350 or over the concave steeple serration region or convex steeple serration region of a turbine rotor steeple.

Cables 70 and 108 are used to move sensor 58 in cam 60. Sensor 58 is mounted in cam 60 on bearing 118, which ensures smooth traversement of sensor 58 in cam 60. Cable 70 is fastened to a first end of sensor 58 and guided at fitting 73 on frame 20, while cable 108 is passed around pulley 270 and fastened to a second end of sensor 58. Sensor 58 is not spring-loaded as is sensor 31 in the sense that sensor 58 will not return to its starting position when cable 70 or 108 is released. This permits the operator to accurately control the speed and direction of sensor 58 as it is pulled by cable 70 away from the base of blade root 350 or pulled by cable 108 toward the base of blade root 350. If, in the operation of sensor 58 by cable 70 or 108, the operator, by referring to data system 12, detects a crack or pit on the surface being inspected, the operator can release cable 70 or 108, causing sensor 58 to stop moving. Once a crack is found, its length may then be determined.

Springs 64, 65 and 67 are attached in series with each other. A first end of the series is fastened to frame 20 by a junction, while a second end of the series is attached to cable 108 at point 116. It may be appreciated by those skilled in the art that the series of springs 64, 65 and 67 may also be attached to cable 70 in a manner similar to the attachment at 116. The tension of springs 64, 65 and 67 is such that they will not interfere with the movement of sensor 58 when either cable 70 or 108 is pulled. During operation of slider assembly 56, cables 70 and/or 108 may become loose. Springs 64, 65 and 67 are designed to tense cables 70 and/or 108 during operation of slider assembly 56, to prevent sensor 58 from moving.

To determine the length of a crack or to control positioning of the root probe to the blade root steeple interface or edge, cam assembly 54 is mounted in slider assembly 56, which can incrementally move cam assembly 54 towards the center of the blade root or rotor steeple, whichever is being inspected. Slider assembly 56 is mounted on shafts 142 and is sized to fit into opening 200 of frame 20. Cable 144 is mounted from end 210 of slider assembly 56 to rim 220 of opening 200. Bar 110 supports cable 66. Spring 146, mounted on cable 144, ensures that slider assembly 56 returns to its initial position. The initial position of slider assembly 56 is such that, when sensor assembly 16 is properly placed within a turbine, sensor 58 will be aligned to measure the concave serration region or the convex serration region of a blade root or rotor steeple, whichever is desired to be inspected. Adjuster screw 271 is used to set start position of slider assembly 56. Operation of slider assembly 56 is controlled by cable 66 and vernier adjuster 104. One end of cable 66 is disposed within adjuster 104 by means known to those skilled in the art. The other end of cable 66 is fed through openings 230 and 232 of frame 20, passes through cable 144, and is internally fastened in slider assembly 56 by means well known in the art.

When a crack is located by sensor 58, the operator rotates adjuster 106 to move cam assembly 54 through cable 66 and slider assembly 56. When cable 66 moves, slider assembly 56 moves cam assembly 54 such that sensor 58, which is mounted in assembly 54, moves generally tangentially to the serration interfaces 700, 702 and 704 as shown in FIG. 4. By following the signals generated on data system 22, the operator will know when the end of the crack has been reached. Comparing the starting position of adjuster 104 and the end position of adjuster 104 by ways known to those skilled in the art, the operator can determine the length of the crack. After the actual crack length is determined, the operator turns adjuster knob 106 counterclockwise, which causes slider assembly 56 to return to its start position. Spring 146, compressed when the crack length is determined, decompresses as knob 106 is turned counterclockwise, ensuring that slider assembly 56 returns to its start position resting on set screw 271.

Cable 62 connects sensor 58 to data system 12. Clamp 120, secured to frame 20 by fasteners 122 and 123, ensures that cable 62 will be properly oriented to prevent lift off of sensor 58 from the area being tested. Cable 112 electrically connects sensor 31 to data system 12.

Controller assembly 18 provides a convenient control apparatus for cables 40, 70 and 108 and vernier adjuster 104. Cables 70 and 108 control the movement of sensor 58, vernier adjuster 104 controls slider assembly 56 movement by cable 66 and cable 40 controls probe holder mount 28 and probe holder 30 movements, as discussed above. Box 114 ensures that cables 40, 66, 70 and 108 do not become entangled. It may be appreciated by those skilled in the art that cables 40, 66, 70, and 108 are of the spring cable type which operate similarly to those found on typical bicycle hand-operated caliper brakes.

Sensor 58, which scans the blade root or trailing edge of a turbine blade or the rotor steeple area of a turbine, is generally of a type capable of detecting the presence of flaws in metal. One type of sensor, which may be adapted for use with the present invention is an eddy current coil.

An alternate arrangement of sensors is possible. As discussed above, it is possible to mount sensors similar to sensor 58 across the lower part of sensor assembly 16. This permits the inspection of several turbine rotor steeple, or rotor steeple, areas and blade root areas with one insertion of sensor assembly 16 (FIG. 4). In this arrangement, turbine blades 400, 402, 404, 406, and 408 (partial) are shown along with their corresponding blade roots 420, 422, 424, 426, and 428 (partial). Turbine blade 400 is mounted, by its respective blade root, between rotor steeples 430 and 432; turbine blades 402, 404, 406, and 408 are similarly mounted by their respective blade roots. A sensor assembly similar to sensor assembly 16 is placed within the turbine in the same manner described above. Here, blade guide 26 would be engaged with trailing edge 416 of blade 406 and probe holder 30 would be engaged with trailing edge 414 of blade 404. Microswitches, similar to microswitches 130 and 131, and magnets 48 and 49 ensure proper sensor assembly 16 placement.

Movement of sensor 492, which is similar to sensor 58 described above, on cam 460 is controlled by spring cables 450 and 454 and cables 452 and 456, connected to cables 450 and 454, respectively, by ordinary means.

Cam 460, similar to cam 60 described above, is formed by cam assembly 440. Bearing 494, similarly sized to bearing 118, allows sensor 492 to glide smoothly within cam 460. Cables 452 and 456 are connected, by ordinary means, to the top and bottom of sensor 492, respectively. Cable 456 is fed around pin 493 and pulley 462 prior to connecting to sensor 492. Cables 450 and 452, when pulled, cause sensor 492 to traverse along cam 460, on bearing 494, away from the base of blade root 422. Cam 460 generally follows the outline of the concave serration region of blade root 422 but could also be positioned to follow the general outline of the convex serration region of blade root 422. Cables 454 and 456, when pulled, cause sensor 492 to traverse along cam 460 towards the base of blade root 422. The overall mechanics of moving sensor 492 is similar to moving sensor 58, as described above.

In this embodiment moving cam assembly 440, when a crack is found, is different than moving cam assembly 54, as described above. Cable 468, passing through spring 470, is fastened to the base of cam assembly 440 at junction 472. Cable 468 is passed around pulley 464 and connected, by ordinary means, to spring cable 466. Pulley 464 is mounted to frame 20 of sensor assembly 16 to ensure proper tangential movement of cam assembly 440 across the concave serration region of blade root 422 towards the center of blade root 422. Cable 466 is controlled by a vernier adjuster (not shown) similar to adjuster 104. As cables 466 and 468 cause the base of cam assembly 440 to move, the top of cam assembly 440 pivots about pivot point 458. Pivot point 458 ensures smooth movement or translation of cam assembly 440 when cables 466 and 468 are pulled. Adjust screw 474 acts as a stop to prevent cam assembly 440 from misaligning over the concave serration region of blade root 422. Similar arrangements are used to move cam assemblies 480, 484, and 488 about pivot points 482, 486, and 490, respectively.

Figure 5:
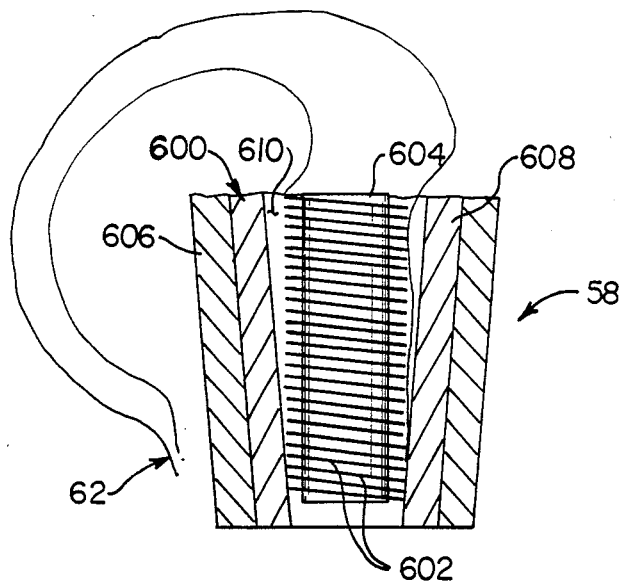
FIG. 5 is a sectional view of a sensor of the turbine inspection system of FIG. 1.
Figure 6:
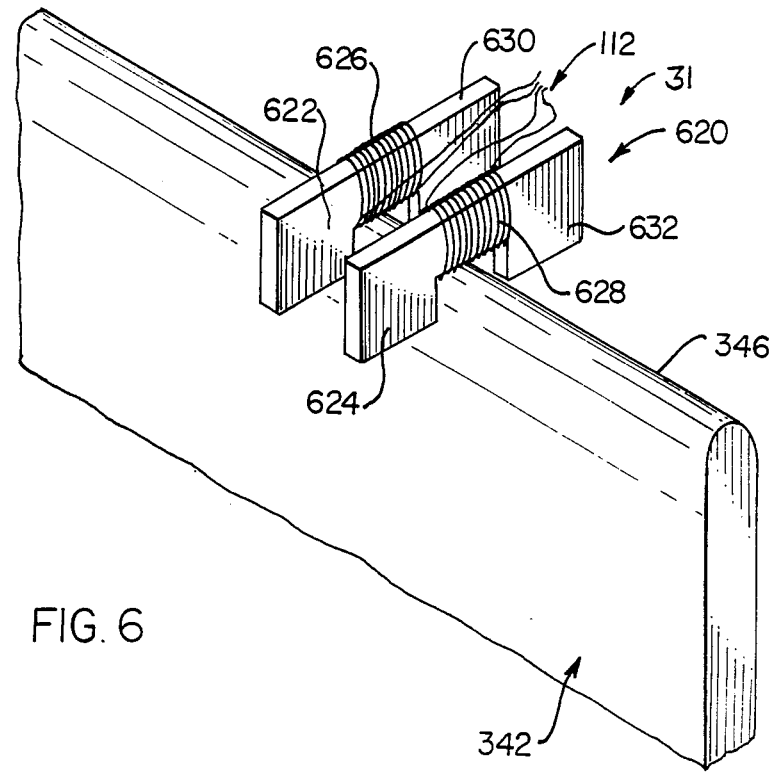
FIG. 6 is an isometric view of another sensor of the turbine inspection system of FIG. 1 shown positioned on a blade of the turbine.

FIGS. 5 and 6 provide details of the construction of the sensors 58 and 31, respectively. Sensor 58 is constructed by wrapping preferably 40 to 50 turns of wire 602 on ferrite pin 604. Shield 600 is then constructed by wrapping a layer of NETIC material, preferably about two mils thick, around the coil. It is preferable that the NETIC material be wrapped in a conical shape so that it engages a portion of the outer surface of wire 602 near the end of the coil which is in contact with the portion of the turbine to be inspected, but not in contact with that portion of wire 602 at the opposite end of the coil. This results in a small air gap 610. An outer layer of CO-NETIC material 606 is then wrapped around NETIC material 608 to complete shield 600.

This conical design aids in focusing the induced eddy current field in order to minimize edge effects from the surrounding geometry and to maximize sensitivity to relatively short-length defects emanating from the edge of the turbine portion being inspected. When the coil is brought close to an edge, the change in geometry affects the eddy current field. The metal, which is being inspected, causes a change in coil impedence, due to edge effect, which is significantly greater than the influence of a small crack-like discontinuity. By positioning shield 600 around the coil, a boundary is created which impedes the magnetic field from spreading radially from the coil. Typically, without a shield, the magnetic field spreads about one and one-half times the diameter of the coil. This shielding, in turn, concentrates or focuses the magnetic flux, from the coil, within a smaller area underneath the coil body improving overall sensitivity to small discontinuities. The conical shape of shield 600 further concentrates the field. FIG. 6 shows the sensor configuration for inspecting the trailing edge of a blade. Sensor 31 includes differential coil assembly 620. Differential coil assembly 620 includes coils 630 and 632. Coil 630 is constructed by wrapping about 40 to 50 turns of wire 626 on U-shaped ferrite piece 622. Similarly, coil 632 is constructed by wrapping about 40 to 50 turns of wire 628 on U-shaped ferrite piece 624. Coils 630 and 632 are then placed in contact with trailing edge 346 of blade 342. As U-shaped ferrite pieces 622 and 624 contain most of the magnetic flux, shielding is not used for sensor 31 as edge effect is generally not of concern. This differential coil arrangement permits a comparison inspection technique as both coils 630 and 632 inspect generally the same area of trailing edge 346, although not simultaneously. After each of coils 630 and 632 inspects a portion of trailing edge 346, the resultant data is displayed on a storage oscilloscope as a complete lissajous pattern and interpreted by the person inspecting the turbine.

An associated method provides apparatus of the type generally described above and provides for positioning the apparatus on the turbine, inspecting the turbine for defects and receiving data relative to the turbine inspection.

Whereas particular embodiments of the invention have been described for purposes of illustration, it will be evident to those skilled in the art that numerous variations of the details may be made without departing from the invention as defined in the appended claims.

What is claimed is:

1. A turbine inspection device comprising:
   support assembly means,
   sensor means on said support assembly means for inspection the turbine for defects, and
   a blade root sensor on said support assembly means adapted to be moveable along a cam adjacent a turbine blade root and shaped to follow a serrated contour of an edge of the turbine blade root for inspecting the blade root of the turbine,
   said support assembly means having attachment means for engaging a portion of the turbine thereby positioning said sensor means and said blade root sensor to facilitate inspection of the turbine and the blade root of the turbine.

2. The turbine inspection device of claim 1 including positioning means cooperating with said support assembly means, said sensor means and said blade root sensor for effecting relative movement between said support assembly means said sensor means and said blade root sensor.

3. The turbine inspection device of claim 2 including said sensor means and said blade root sensor having output means for providing data relative to said inspection of the turbine by said sensor means and said inspection blade root sensor.

4. The turbine inspection device of claim 3 including said positioning means having cable means for effecting said relative movement between said support assembly means, said blade root sensor and said sensor means.

5. The turbine inspection device of claim 4 including said sensor means having a first sensor means for inspecting the trailing edge of a blade of the turbine.

6. The turbine inspection device of claim 5 including said sensor means having a second sensor means for inspecting the rotor steeple of the turbine.

7. The turbine inspection device of claim 4 including said sensor means and said blade root sensor having eddy current sensor means.

8. A method for inspecting turbines comprising:
providing a turbine inspection device which includes support assembly means, sensor means on said support assembly means for inspecting the turbine for defects and a blade root sensor on said support assembly means adapted to be moveable along a cam adjacent a turbine blade root and shaped to follow a serrated contour of an edge of the turbine blade root for inspecting the blade root of the turbine, with said support assembly means having attachment means for engaging a portion of the turbine thereby positioning said sensor means and said blade root sensor to facilitate inspection of the turbine,
positioning said support assembly means on the turbine,
inspecting the turbine with said sensor means,
inspecting a blade root of the turbine with said blade root sensor, and
receiving data from said sensor means and said blade root sensor relative to said inspection of the turbine and a blade root of the turbine.

9. The method of claim 8 including moving said sensor means and said blade root sensor relative to the turbine and said support assembly means thereby inspecting different portions of the turbine.

10. The method of claim 9 including moving said sensor means and said blade root sensor with cable means.

11. The method of claim 9 including inspecting the trailing edge of a blade of the turbine.

12. The method of claim 9 including inspecting the rotor steeple of a turbine.

13. The method of claim 9 including electromagnetically inspecting the turbine.

14. A turbine inspection device comprising:
support assembly means which includes attachment means for engaging a blade of the turbine,
a blade root sensor slidably mounted on said support assembly means and adapted to be movable along a cam defined by said support assembly means and movable along a serrated edge of the blade root of a blade of the turbine to be inspected when said support assembly means is engaged with a blade of the turbine, and
positioning cable means cooperating with said support assembly means and said blade root sensor for effecting said movement between said support assembly means and said blade root sensor,
said blade root sensor including output means for providing data relative to said inspection of the blade root of a blade of the turbine by said blade root sensor.

15. The turbine inspection device of claim 14 including:
a first sensor means for inspecting the trailing edge of a blade of the turbine, and
a second sensor means for inspecting the rotor steeple of the turbine.

16. The turbine inspection device of claim 14 including and said blade root sensor eddy current sensor means.

* * * * *